United States Patent
Gross (10) Patent No.: US 11,540,770 B2
(45) Date of Patent: Jan. 3, 2023

(54) SYSTEM FOR DETERMINING A SLEEP QUALITY, SENSOR ARRANGEMENT FOR SUCH A SYSTEM, AND SLEEP OR REST FURNITURE COMPRISING SUCH A SYSTEM

(71) Applicant: DewertOkin GmbH, Kirchlengern (DE)

(72) Inventor: Josef Gross, Friesoythe (DE)

(73) Assignee: Dewertokin Technology Group Co., Ltd, Jiaxing (CN)

( * ) Notice: Subject to any disclaimer, the term of this patent is extended or adjusted under 35 U.S.C. 154(b) by 410 days.

(21) Appl. No.: 16/613,696

(22) PCT Filed: May 15, 2018

(86) PCT No.: PCT/EP2018/062584
§ 371 (c)(1),
(2) Date: Nov. 14, 2019

(87) PCT Pub. No.: WO2018/210856
PCT Pub. Date: Nov. 22, 2018

(65) Prior Publication Data
US 2020/0289052 A1   Sep. 17, 2020

(30) Foreign Application Priority Data
May 15, 2017   (DE) ..................... 20 2017 102 920.4

(51) Int. Cl.
*A61B 5/00* (2006.01)

(52) U.S. Cl.
CPC .......... *A61B 5/4815* (2013.01); *A61B 5/0022* (2013.01); *A61B 5/6891* (2013.01);
(Continued)

(58) Field of Classification Search
CPC ... A61B 5/4815; A61B 5/0022; A61B 5/6891; A61B 2560/0247; A61B 2560/0252;
(Continued)

(56) References Cited

U.S. PATENT DOCUMENTS

| 2009/0121826 A1 | 5/2009 | Song et al. |
| 2009/0177327 A1 | 7/2009 | Turner et al. |

(Continued)

FOREIGN PATENT DOCUMENTS

| DE | 202014009784 | 5/2015 |
| DE | 202016105634 | 5/2017 |
| EP | 3 138 480 | 3/2017 |

OTHER PUBLICATIONS

Machine Translation of DE 202014009784 U1 (Year: 2014).*

(Continued)

*Primary Examiner* — David J. McCrosky
(74) *Attorney, Agent, or Firm* — Henry M. Feiereisen LLC (57) ABSTRACT

The invention relates to a system for determining a value representing a sleep quality, wherein the system has an evaluation device (10) for connecting to at least one sensor (11), which can be coupled to a piece of sleep or rest furniture for detecting vibrations, movement and/or sound in order to extract physiological data (12) of at least one person using the piece of sleep or rest furniture. The system is characterized in that at least one additional sensor (21) is provided on the sleep or rest furniture or in an environment of the sleep or rest furniture, which sensor is designed for detecting environmental parameters (5).

14 Claims, 4 Drawing Sheets

(52) U.S. Cl.
CPC .......... *A61B 2560/0247* (2013.01); *A61B 2560/0252* (2013.01)

(58) Field of Classification Search
CPC ... A61B 5/4806; A61B 5/4809; A61B 5/4812; A61B 5/4818
See application file for complete search history.

(56) References Cited

U.S. PATENT DOCUMENTS

2014/0378787 A1    12/2014  Brumback et al.
2015/0130595 A1*   5/2015   Hille .................. G08C 23/04
                                              340/12.5

OTHER PUBLICATIONS

International Search Report issued by the European Patent Office in International Application PCT/EP2018/062584 dated Jul. 16, 2018.
German Search Report dated Jul. 27, 2017 with respect to corresponding German patent application No. 20 2017 102 920.41.
Translation of German Search Report dated Jul. 27, 2017 with respect to corresponding German patent application No. 20 2017 102 920.41.

* cited by examiner

SYSTEM FOR DETERMINING A SLEEP QUALITY, SENSOR ARRANGEMENT FOR SUCH A SYSTEM, AND SLEEP OR REST FURNITURE COMPRISING SUCH A SYSTEM

CROSS-REFERENCES TO RELATED APPLICATIONS

This application is the U.S. National Stage of International Application No. PCT/EP2018/062584, filed May 15, 2018, which designated the United States and has been published as international Publication No. WO 2018/210856 and which claims the priority of German Patent Application, Serial No. 20 2017 102 920.4, filed May 15, 2017, pursuant to 35 U.S.C. 119(a)-(d).

BACKGROUND OF THE INVENTION

The invention relates to a system for determining a value representing a sleep quality, wherein the system comprises an evaluation device for connection to at least one sensor, which can be coupled to a piece of sleep or rest furniture for detecting vibrations, movement and/or sound, in order to extract physiological data of at least one person using the piece of sleep or rest furniture. The invention also concerns a piece of sleep or rest furniture, in particular a bed, with such a system. The invention also relates to a sensor arrangement for use in such a system.

In the clinical field, monitoring devices are known to monitor the respiration and/or cardiac activity of a patient during sleep in order to be able to intervene in questionable cardiac function and circulation parameters.

Meanwhile, devices for monitoring sleep status on the basis of physiological parameters are also commercially available for non-clinical purposes. These devices, which are placed on a nightstand for example, capture sounds and/or motion during sleep using microphones and/or cameras. A sleep state is derived from the recorded information, the temporal course of which is recorded. The recorded sleep progress can be called up and evaluated afterwards. It can provide information on how deep and restful sleep has been, for example by giving a value representing a sleep quality on a given scale.

In addition to systems that use cameras and/or microphones, there is also a known sensor-based system in which a pressure-sensitive sensor strip is placed over the mattress and this sensor strip is connected to a mobile phone (smartphone) that records the sensor data. From the sensor data a heart rate and a respiratory rate are derived.

In order to summarize the results clearly, it is known that from the sensor data recorded as continuously as possible during a sleep period, e.g. one night, a value is determined that represents the sleep quality. In practice, however, it has been shown that such a sleep quality value, which is based on sensor data relating to the vibration or movement of parts of the bed, such as a mattress, in some cases does not correctly reflect the recovery value of sleep for the person concerned.

It is the object of the present invention to improve an initially mentioned system for recording the sleep quality on the basis of the sensor data in order to achieve a greater correspondence between the determined value and the subjectively perceived sleep quality.

SUMMARY OF THE INVENTION

This object is solved by a system, a piece of sleep or rest furniture with such a system and a sensor arrangement for such a system with the features of the respective independent claim. Advantageous arrangements and further developments are the subject matter of the dependent claims.

A system according to the invention of the type mentioned above is characterized in that, in addition to the sensor which can be coupled to the piece of sleep or rest furniture to detect vibrations, movement and/or sound and the signals of which are used to determine physiological data of at least one user of the piece of sleep or rest furniture, at least one further sensor is provided on the piece of sleep or rest furniture or in an ambient environment of the piece of sleep or rest furniture, which sensor is designed for detecting ambient parameters.

The invention is based on the knowledge that a subjectively experienced and objectively existing sleep quality cannot only be derived from a breathing, heart rate and/or movement pattern of the resting person but is also significantly influenced by ambient influences. The additional sensor according to the invention, which is set up to detect at least one ambient parameter, enables the ambient influence to be measured and this ambient influence to be taken into account during sleep at the value determined for sleep quality.

In an advantageous embodiment of the system, at least one further sensor is a temperature sensor, a humidity sensor, an airborne sound sensor and/or a brightness sensor. These sensors are suitable for recording ambient influences that directly influence the sleep quality, namely the ambient temperature, the (air) humidity of the environment, the brightness and a volume level.

The evaluation device determines physiological data of at least one person using the system from signals from at least one sensor. The specific physiological data include, for example, a respiratory rate, a heart rate (pulse) and/or movement pattern of the person(s). Preferably, an evaluation circuit uses the signals from at least one other sensor to determine ambient data that digitally reflect the existing ambient parameters.

In principle, the ambient data mentioned above are recorded and made available in electronic form or in data form for further use and subsequent processing. The ambient data can be used to determine the sleep quality of at least one person. Preferably, this is carried out by an evaluation device, as mentioned at the beginning. Alternatively, a number of evaluation devices are provided which receive the ambient data.

An arrangement with single-user furniture would be conceivable, alternatively with multi-user furniture, wherein each piece of furniture or multi-user furniture has its own evaluation device and receives the ambient data from a common sensor arrangement. The system for determining a value representing the sleep quality comprises, in accordance with this arrangement, the number of single-user furniture and/or multi-user furniture, as well as the at least one sensor arrangement.

All types of seating, reclining and resting furniture that are designed to accommodate one person in normal operating conditions can be considered as single-user furniture. These are, for example, single beds or armchairs. Multi-user furniture can be composed of single beds, double beds or beds designed to accommodate more than one person, such as sofas or double beds.

In a further advantageous embodiment of the system there is a (superordinate) evaluation and display unit which is coupled to the evaluation device and the evaluation circuit and is adapted to evaluate the physiological data and the ambient data and to determine the value representing the sleep quality. A (usually already existing) mobile device, e.g. a smartphone or a tablet computer, can be used especially advantageously as an evaluation and display unit.

The evaluation and display unit can also be used to display the physiological data and/or the ambient data of one or more previous sleep periods, e.g. in statistically processed form. Furthermore, a correlation between the physiological data and the ambient data can be made in the evaluation and display unit. The correlation makes it possible to determine individual influences of the ambient parameters on the physiological data. In this way, the person using the system, hereinafter also referred to as the user, can be given instructions on how ambient influences can best be influenced in order to achieve a restful sleep. Furthermore, it may be provided that the evaluation and display unit calculates an identification number from the ambient data in order to clarify to the user in a concise manner the ambient influences of the previous sleep period and to characterize the influence of the ambient parameters on the sleep quality.

In a further advantageous embodiment of the system, the at least one further sensor is integrated in a housing together with the evaluation circuit and a transmission unit for outputting the ambient data. This creates a compact (additional) unit to measure the ambient parameters and make them available for further consideration.

If the evaluation circuit is designed as a compact additional unit with its own housing, the transmission unit is designed as a wired transmission unit and the ambient data is transmitted to the evaluation device via a wire. Alternatively, the data is transmitted wirelessly, for example by means of a radio link, and the ambient data is now transmitted wirelessly to the evaluation unit.

The fact that at least one sensor with an evaluation circuit is arranged in its own housing has the advantage that the respective sensor can detect an unaltered value. Light and humidity sensors are thus usefully arranged on the outside of the furniture or spatially separated from the furniture for design reasons. A conceivable spatially separate arrangement would be on the nightstand, for example. A spatial separation does not separate the system according to the invention. Rather, the system according to the invention comprises all units, furniture and equipment which are intended to determine the sleep quality and are functionally related to each other.

A sensor arrangement according to the invention for detecting ambient parameters of a piece of sleep or rest furniture is characterized in that the sensor arrangement has at least one sensor for measuring an ambient parameter, an evaluation device for evaluating sensor signals and a transmission unit for outputting the measured ambient parameter in the form of digital ambient data.

The above-mentioned sensor arrangement thus independently and autonomously determines one or more ambient parameters of a bed, evaluates them and transmits them in digital and thus easily evaluable form, for example to the evaluation device of a system for determining sleep quality. The ambient influences can be taken into account without having to connect sensors directly to the evaluation device. The sensor arrangement is thus also suitable for retrofitting existing systems to determine sleep quality. As a rule, these already have a usable interface for receiving the transmitted information in digital form. An extension of the functionality, by which the ambient parameters are taken into account when determining the sleep quality, is then possible, for example, by adding the above-mentioned sensor arrangement and software adaptation ("firmware update") of the existing evaluation device.

The at least one other sensor is preferably a temperature sensor, a humidity sensor, an airborne sound sensor and/or a brightness sensor. Another preferred option is that the transmission unit is adapted for wireless transmission of digital ambient data, for example using the BLUETOOTH® and/or Wireless Local Area Network (WLAN) protocol. These data transmission paths are particularly advantageous if a connection is provided with a mobile device that is used as an evaluation and display unit.

A piece of sleep or rest furniture, in particular a bed, in accordance with the invention is finally characterized by the use of a system of the type described above. The other sensor that is used to determine the ambient parameters is particularly preferably part of the aforementioned sensor arrangement. This results in the advantages described in connection with the system or the sensor arrangement.

In an advantageous further development, the piece of sleep or rest furniture has an electromotive furniture drive having a control unit and at least one adjustment drive. The evaluation device and/or the sensor arrangement of the system for determining the sleep quality are preferably integrated into the control unit of the electromotive furniture drive. In this way, components such as a power supply unit and/or data transmission units can be effectively shared.

In principle, according to other embodiments, several evaluation devices and/or evaluation circuits can be provided, which are integrated into the system for determining a value representing the sleep quality and thus integrated therein. The piece of sleep or rest furniture can also have such a system with several evaluation devices and/or evaluation circuits.

It is essential that the at least one evaluation circuit and/or the at least one sensor in the system or in the furniture is networked in such a way that an evaluable signal for determining the value representing the sleep quality is provided by the at least one sensor. The evaluable signal is provided via a transmission path. Said transmission path is either wired or alternatively formed in a wireless manner.

Thus it is conceivable that a number of sensors are arranged in a separate housing. It is also conceivable that existing devices of already existing equipment is used as a sensor. Such devices can be formed, for example, by the microphone, the camera, the light sensor or the like of a smartphone or tablet computer. A program running on it queries the input variables of the respective device and sends these preferably wirelessly and in data form either to the evaluation device or to the evaluation circuit. In order to generally reduce the data stream and/or the energy consumption, it is planned that the acquisition of the sensor-based input variables, but at least the transmission of the data, does not take place permanently but in individual time periods.

Other devices can be arranged fixed to the building and, for example, have a humidity sensor.

Further devices are designed as plug devices for insertion into a mains socket and are designed for recording and transmitting sensor values or sensor data representing ambient parameters such as brightness, humidity, sound or the like. The transmission is preferably wireless to the evaluation device and/or to the evaluation circuit.

Other devices are primarily designed for a different purpose and are adapted, for example, as chargers for inductive and wireless charging of the battery storage of a smartphone, for example. According to the invention and one variant, the at least one sensor is now integrated in this device. The particular advantage is that such devices already have a wired connection to the power supply, which can also be used to power the at least one sensor. This reduces the variety of components and devices and also simplifies assembly.

In principle, all the evaluation devices, evaluation circuits and/or equipment mentioned at the beginning can be arranged on the furniture, in the furniture or in the immediate vicinity of the furniture, so that the system for determining the sleep quality is given.

It is also possible to improve and/or supplement the quality of the sleep quality determined, particularly qualitatively but also quantitatively. Quantitative improvement characteristics are formed by further values, which are expressed in numerical values or in events. In particular, they are based on measured variables of at least one other sensor. Thus the user can also receive additional information representing the sleep quality, from which he can either derive his own findings or wherein the system provides or suggests concrete facts for improving the sleep quality. An example of such a proposal would be the adaptation of the room temperature.

BRIEF DESCRIPTION OF THE DRAWING

The invention will be explained in the following by means of embodiment examples shown in the drawings, wherein.

DETAILED DESCRIPTION OF PREFERRED EMBODIMENTS

Figure 1:
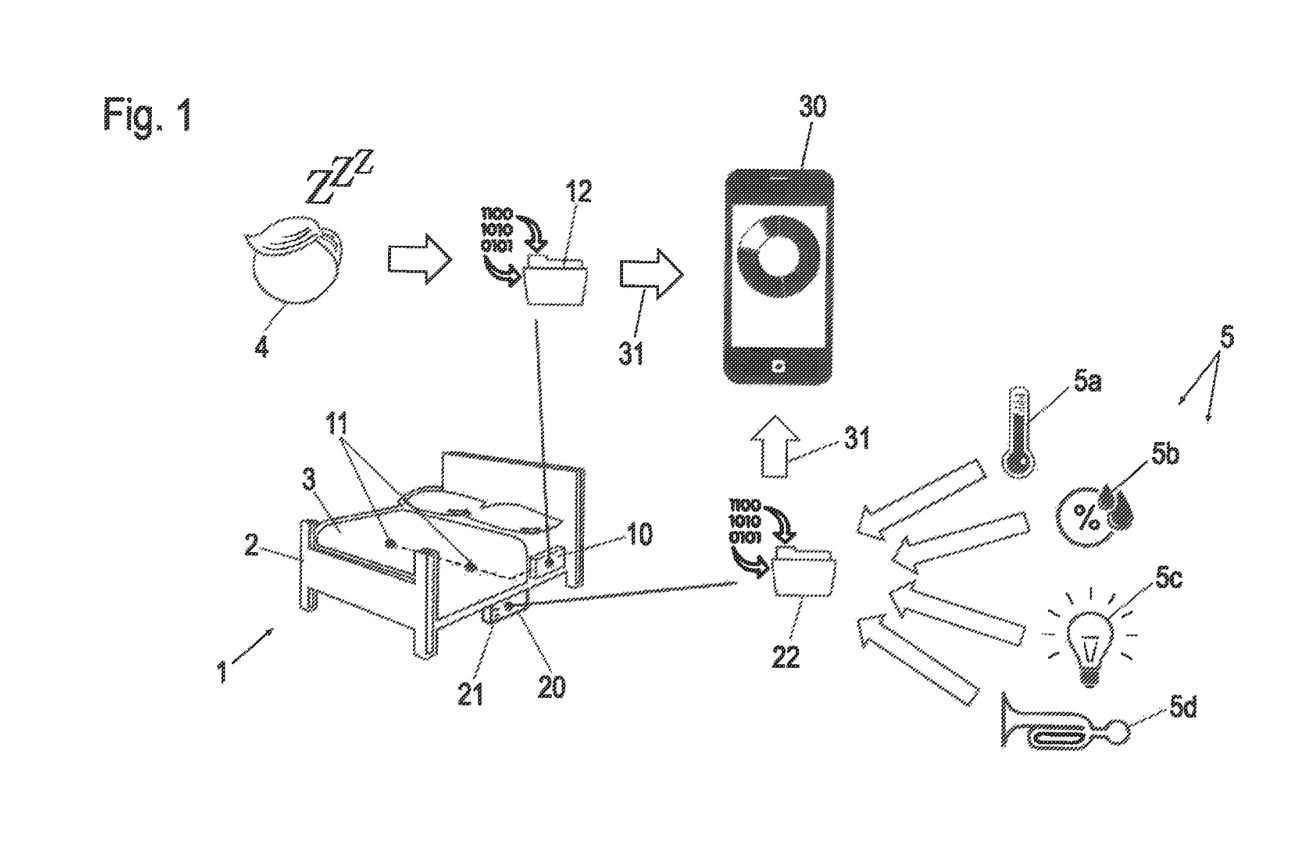
FIG. 1 shows a schematic representation of a first embodiment example of a system for determining sleep quality arranged on a bed.

FIG. 1 shows a schematic representation of a bed 1 as an example of sleeping furniture with a system for determining a value representing sleep quality. For the sake of simplicity, the value representing sleep quality will be referred to as sleep quality in the following.

Bed 1 has a frame 2 with a lying surface 3. For example, bed 1 is designed as a double bed, which can accommodate one or two persons 4. The following versions are transferable to a single bed for only one person 4.

On frame 2 of bed 1 there is an evaluation device 10 which is coupled to sensors 11. As an example, two sensors 11 are shown, which are each arranged in a left and a right half of the bed in the area of the lying surface 3. The sensors 11 are suitable for detecting vibrations, movement and/or sound. Sensors 11 can, for example, be attached to a frame component or to a lying surface part such as a slatted frame in the area of lying surface 3 on bed 1. The fastening can be a screw or rivet or adhesive connection, or also a snap or clamp connection, for example with the help of a spring clamp which embraces the corresponding frame component or a part of the slatted frame. A recording device can be used to record at least one sensor 11.

Sensors 11 can be designed as piezoelectric elements, electromagnetic elements or electromechanical elements, for example, and are sensitive to vibrations of the supports on which they are mounted. Another suitable sensor type for sensors 11 is an electromechanical sensor, e.g. designed as a micromechanical acceleration sensor.

The vibrations and movements detected by the sensors 11 include in particular structure-borne sound transmitted by person 4 or persons 4 to the sensors 11 via elements of the lying surface 3, e.g. a mattress. In particular, structure-borne sound also includes low-frequency vibrations and designs of sensor 11 whose frequency is in the Hertz or sub-Hertz range.

The sensors 11 are connected to the evaluation unit 10 via a sensor cable. If required, a power supply for the sensors 11 is provided via the sensor cable. In addition, signals output by the sensors 11 are forwarded to the evaluation unit 10. Alternatively, the sensors 11 can be coupled to the evaluation unit 10 via wireless connections, e.g. a radio connection. In this case, each of the sensors 11 is equipped with its own power supply, for example in the form of a rechargeable battery.

The bed 1 shown in FIG. 1 has, for example, only one sensor 11 for each side of the bed and thus each person 4. Several sound or vibration transducers can be combined in one sensor or different sensors, wherein, for example, a piezoelectric and an electromagnetically operating sensor are arranged at the same or different positions. A combination of different sensor types makes it possible to record and analyze a particularly broad frequency spectrum, since different sensor types are characterized by different frequency ranges.

The evaluation device 10 comprises components which make it possible to deduce certain body functions of a person 4 in bed 1 from the signals transmitted by the sensors 11. In particular, the evaluation device is designed to determine physiological parameters of the person(s) 4 from the signals of the sensor 11. Such parameters concern for example heart and circulation functions and include, for example, a heart rate and a respiratory rate. It can also be determined whether the person(s) 4 snores or are snoring. In addition, movements of person(s) 4 are recorded.

In the evaluation device 10 at least one preprocessing of the signals of the sensors 11 is carried out in such a way that the physiological parameters of the person(s) 4 using the bed 1 are determined on the basis of the signals of the sensors 11. For this purpose, the evaluation unit 10 has e.g. (signal) amplifiers and filter units. For example, a signal-strength-dependent gain control (Automatic Gain Control) can be provided. Low pass or bandpass filters with suitable cut-off frequencies are used to eliminate interference frequencies. The signals are preferably processed using a digital signal processor (DSP). In particular, it can be provided to subject the signals to a spectral analysis, e.g. by a fast Fourier transformation (FFT Fast Fourier Transform), in order to be able to analyze frequency components contained in the course of the signals. The obtained spectra can also be filtered, for example by only processing frequency components with a specific minimum amplitude and discarding others.

The determined physiological parameters are output as data, hereinafter referred to as physiological data 12. The physiological data 12 can also be temporarily stored in the evaluation unit 10, so that output to a further processing unit can be continuous or occur in blocks.

In the embodiment example shown in FIG. 1, the evaluation device 10 is connected to an evaluation and display unit 30, which optionally carries out a further evaluation of the physiological data 12, but in any case its visualization. In an advantageous embodiment, which is also symbolized in FIG. 1, the evaluation and display unit 30 is a mobile telephone which is designed as the evaluation and display unit 30 by executing a corresponding program ("App").

Data transmission 31 to the evaluation and display unit 30 is preferably via a wireless connection, for example via a WAN or Bluetooth® connection.

The evaluation and display unit 30 also takes over a further evaluation of the physiological data 12 in the embodiment example shown in order to convert them into a value representing the sleep quality.

According to the application, this sleep quality value shall not be calculated exclusively from physiological data 12, but shall take into account measured ambient influences such as ambient temperature 5a, ambient humidity 5b, ambient brightness 5c and ambient volume 5d.

These ambient influences are symbolized in the right part of FIG. 1 and are collectively referred to as ambient parameters 5. The measurement and evaluation of the ambient parameters 5 is carried out in a sensor arrangement 20, which is also positioned in the area of bed 1, as shown in the example on the frame 2 of bed 1.

The sensor arrangement 20 has at least one sensor. In this case, there are several other sensors 21 which are suitable for measuring the ambient parameters 5. The measured ambient parameters 5 are evaluated in the sensor arrangement 20 and provided in the form of digital ambient data 22 by the sensor arrangement 20.

Similar to the evaluation device 10, the sensor arrangement 20 can have a memory in which the ambient data 22 are stored for a longer period of time. They can be called up by the sensor arrangement 20 in the shown digital form (quasi) continuously or in the form of data blocks.

The ambient parameters 5 are preferably recorded continuously, for example with one or more measured values per second or minute. The ambient data 22 can include corresponding time series, optionally in compressed form. In an alternative embodiment it is planned to carry out a pre-evaluation of the ambient parameters 5 in the sensor arrangement 20 already, in such a way that, for example, an averaging over longer periods of time takes place. Rapid temperature fluctuations, for example, are unlikely, so that it is sufficient with regard to the ambient temperature 5a to provide an average temperature value only for every half hour or every hour, for example.

Another form of data preprocessing, which can already be carried out in sensor arrangement 20, relates to a comparison with a threshold value. The ambient noise level 5d, for example, usually only affects the sleep of person 4 if it is above a pre-settable or adjustable threshold value. Thus, instead of a continuous transmission of data of the ambient volume 5d, it can be provided to only record volume events at which the ambient volume 5d exceeds a certain value.

The ambient data 22—comparable to the physiological data 12—are transmitted to the evaluation and display unit 30, for example via a wireless data transmission 31. The value for the sleep quality is then calculated on the basis of an evaluation of both the physiological data 12 as well as the ambient data 22.

Furthermore, a correlation can be made between the physiological data 12 and the ambient data 22. The correlation makes it possible to determine individual influences of the ambient parameters 22 on the physiological data 12. In this way, the person 4 can be given advice on how best to influence ambient influences in order to achieve a restful sleep. In order to clearly illustrate the ambient influences of the previous sleep period to person 4, an indicator can be calculated from the ambient data 22 that summarizes the influence of the ambient parameters 5 on sleep quality.

Figure 2:
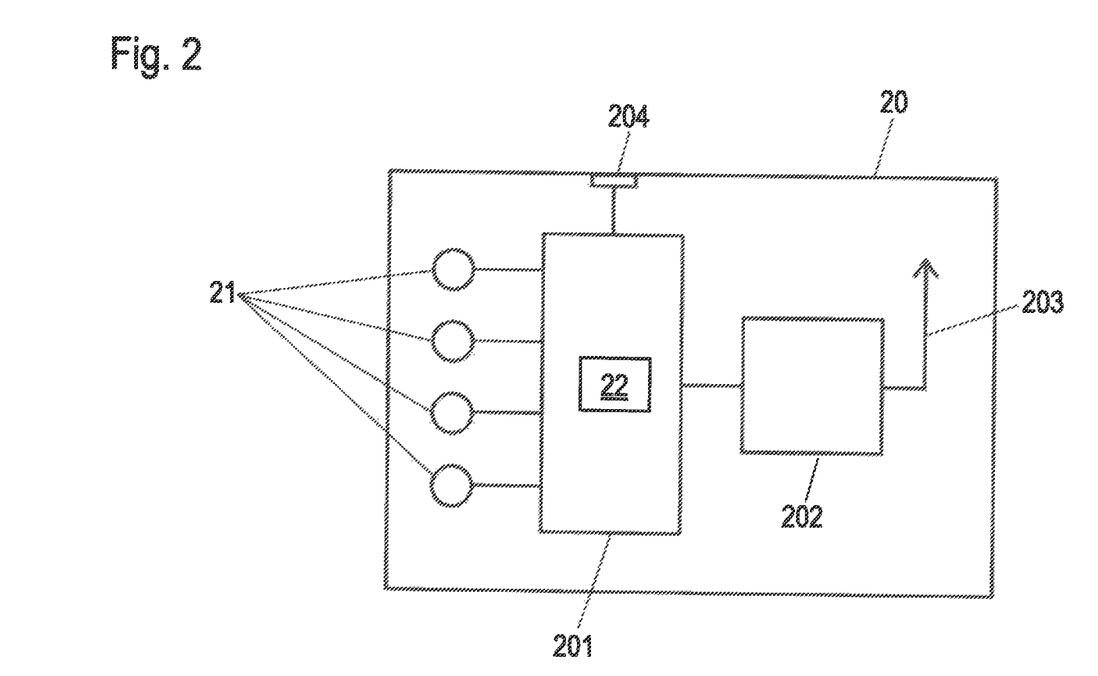
FIG. 2 shows a schematic block diagram of a sensor arrangement of the system shown in FIG. 1.

FIG. 2 shows an embodiment of a sensor arrangement 20, as it can be used in FIG. 1, in a schematic block diagram.

The sensor arrangement 20 comprises a plurality, here four further sensors 21 for ambient parameters 5. The further sensors 21 are present at or arranged in a housing of the sensor arrangement 20, wherein corresponding openings are present at the housing so that the ambient influences of the sensor 21 can also be measured correctly or at least in a correctable manner.

The further sensors 21 are connected to an evaluation circuit 201, which evaluates the usually analog signals of the other sensors 21, independently of their mounting location. The evaluation may include filtering and/or pre-amplification and/or linearization. The signals preprocessed in this way are digitized, for example in an analog-to-digital converter that can be part of a microcontroller of evaluation circuit 201. The digitized information can be further preprocessed in the sensor arrangement 20, for example by forming time averages. As a result, the ambient data 22 described above are generated and stored in the sensor arrangement 20, for example in the form of time series and/or events bearing a time stamp. A power supply connection 204 is provided for the power supply of the sensor arrangement 20. This can be set up as a DC voltage connection, e.g. as a USB (Universal Serial Bus) connection for connection to a plug-in power supply unit or to the evaluation unit 10.

A transmission unit 202 is coupled to the evaluation circuit 201, in the example shown for wireless data transmission using an antenna 203. The transmission unit 202 can, for example, be set up for transmission according to the WLAN or BLUETOOTH® standard. As mentioned in connection with FIG. 1, the transmission of ambient data 22 can be continuous (quasi) or in blocks. For example, during a sleep period, e.g. a night, information about the last hour can be transmitted.

Preferably, the sensor arrangement 20 is, for example, equipped with a real-time clock as part of evaluation circuit 201, so that the mentioned time stamps can be applied. In order to make the use and setup of the sensor arrangement 20 as user-friendly as possible, it may be provided to synchronize the real-time clock automatically with the evaluation and display unit 30 as part of a data connection.

As is also mentioned in connection with FIG. 1, the sensor arrangement 20 can be equipped with a threshold value detection as further preprocessing of the measured information, so that an event-based logging within the ambient data only takes place if the determined data values lie outside a predefinable range. It can be provided in this case to transmit the limits of this predefinable range to the sensor arrangement 20 also in communication with the evaluation and display unit 30. The evaluation and display unit 30 can also be used to start the recording of ambient data 22 and to stop the recording of ambient data 22. For example, it may be planned to determine the beginning and end of a sleep period on the basis of the physiological data 12 and to instruct the sensor arrangement 20 to start or stop logging the ambient parameters 5 at appropriate times.

Figure 3:
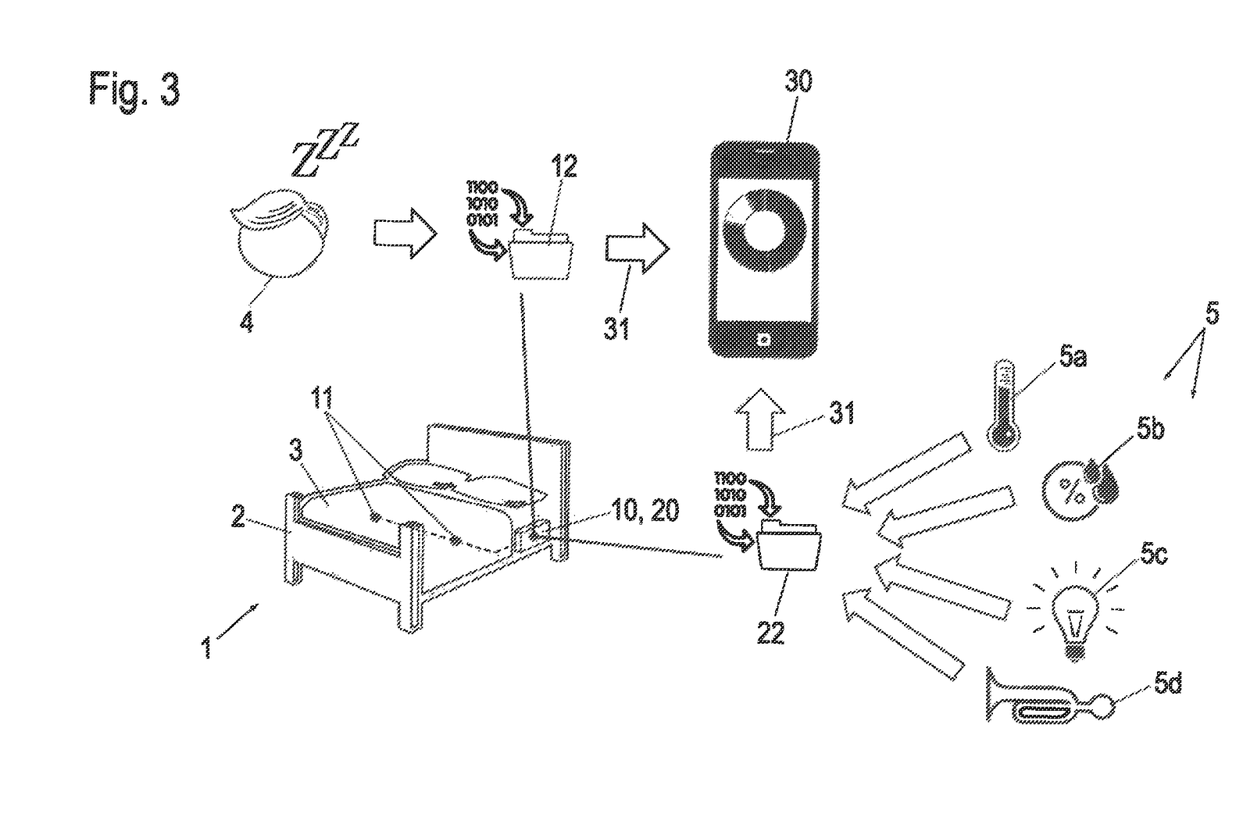
FIG. 3 shows a second embodiment example of a system for determining sleep quality.

FIG. 3 shows another embodiment example of a system for determining sleep quality, arranged on a bed 1 in the same way as FIG. 1. Identical reference numerals mark identical or equivalent elements in this and the following figure.

With regard to the basic structure, the example shown in FIG. 3 is comparable to that shown in FIG. 1, which is why explicit reference is made to the description of FIG. 1. In contrast to the example of FIG. 1, the evaluation unit 10 is integrated together with the sensor arrangement 20 in a housing in the example of FIG. 3. This offers the advantage that certain components, which would otherwise have to be redundantly present in the evaluation unit 10 and the sensor arrangement 20, are only simply available. For example, the physiological data 20 and the ambient data 22 can be transmitted via a shared transmission unit in the embodiment example of FIG. 3. A power supply unit can also be used for both components.

In a further development of the arrangement, it can also be planned to integrate both the evaluation device 10 and the sensor arrangement 20 with a control device for an electromotive furniture drive which is installed in bed 1. In this way, synergy effects can be used even more efficiently.

Figure 4:
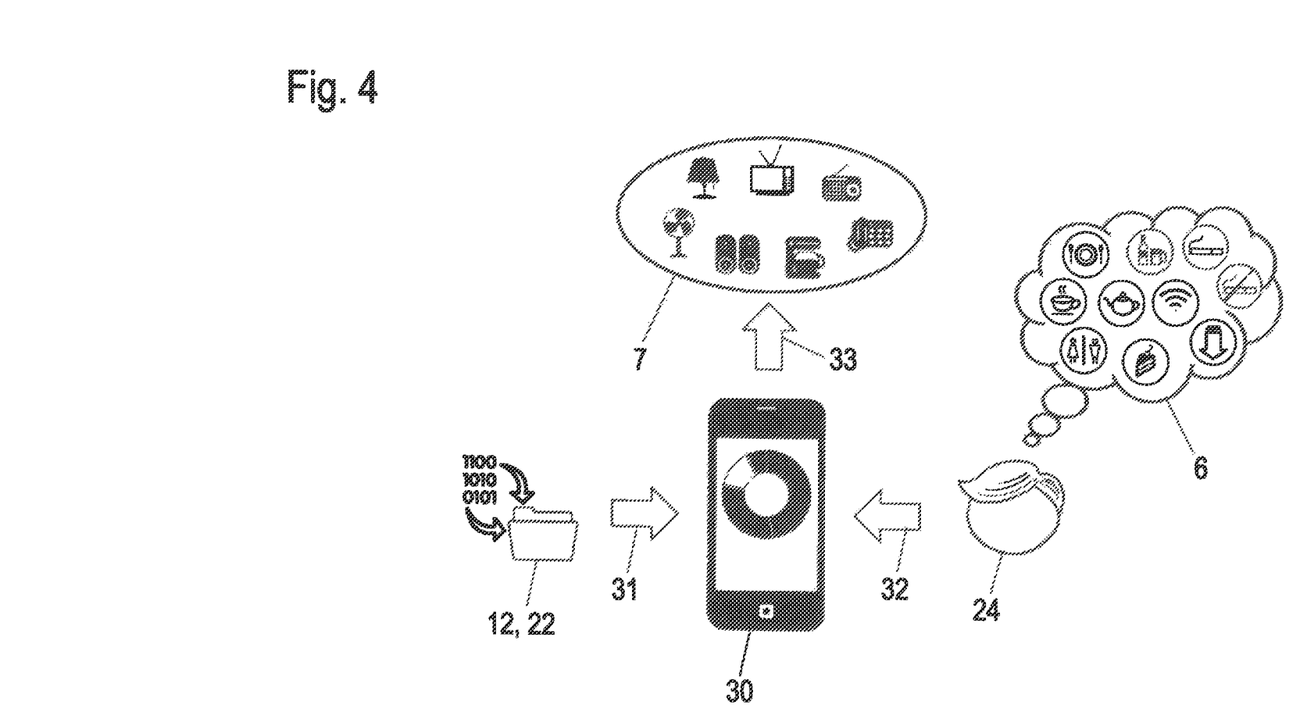
FIG. 4 shows a schematic representation of a supplement to the systems shown in FIGS. 1 and 3.

FIG. 4 finally shows a further development of the system, which can be used in the example of FIG. 1 as well as in the example of FIG. 3. For space reasons, neither the evaluation device 10 nor the sensor arrangement 20 is displayed by the system for determining sleep quality, but only the transmission of physiological data 12 and ambient data 22 to the evaluation and display unit 30.

In the example in FIG. 4, in addition to the evaluation of the measured ambient data 22, it is provided to transfer further ambient influences 6 from person 4 via a manual data input 32 to the evaluation and display unit 30. Information on, for example, the consumption of food, drink, stimulants or media shortly before the beginning of the sleep period or in the course of the previous day is also important data for assessing the sleep quality. These cannot be measured by the sensor arrangement 20 but can be entered manually in the manner shown. Furthermore, information on health status or the like can be provided manually in this way.

As explained in connection with the ambient data 22 collected automatically by the other sensors, the manually entered data can also be correlated with the physiological data in order to determine which of the other ambient influences 6 have an effect on sleep quality and to what extent. If clear correlations are observed on the basis of correspondingly high correlation coefficients, the evaluation and display unit 30 of person 4 can in turn provide indications of this in order to specifically use or reduce or avoid these further positive or negative ambient influences 6 in the future.

Furthermore, a control of external devices 7 by the evaluation and display unit 30 is shown in the example of FIG. 4. For example, several electronic devices are shown here, e.g. a lamp representing one or more lighting devices and a fan representing a heating or air conditioning system. In addition, devices for entertainment and communication electronics as well as a coffee machine are shown as substitutes for one or more kitchen machines.

In the further development of the system, a control possibility of the evaluation and display unit 30 via a control channel 33 for at least one of these external devices 7 is assumed, wherein the corresponding device 7 is controlled depending on the measured physiological data 12 and/or ambient data 22.

For example, it is conceivable that, in response to an ambient brightness 5c and/or color temperature which is not within a comfort range for the corresponding user 4, the evaluation and display unit 30 controls at least one lighting device and/or a darkening device (e.g. motorized movable blind) in such a way that a preferred ambient brightness 5c and/or color temperature is set in the region of the bed 1.

Furthermore, it is conceivable that heating and/or air conditioning devices are controlled in order to bring the ambient temperature 5a into an advantageous range. This range does not necessarily have to be defined in advance, but can also be selected dynamically on the basis of the physiological data 12 of existing sleep behavior.

In the evaluation of the physiological data 12 and the ambient data 22, sleep phases can also be detected, for example a deep sleep phase or a wake-up phase. If, for example, the detected wake-up phase lies within a time range that is specified for getting up, consumer electronics devices can also be switched on to initiate a gentle wake-up, e.g. with music. If an actual wake-up is detected on the basis of the physiological data, kitchen appliances such as a coffee machine can be switched on, for example.

If the described system is used in conjunction with a piece of sleep or rest furniture equipped with an electromotive furniture drive, the evaluation and display unit 30 can also be coupled to a control unit of the electromotive furniture drive via control channel 33. The evaluation and display unit 30 can then control actions of the furniture drive. For example, it can be provided that an adjustment motor of the electromotive furniture drive is activated when certain sleep states are detected, e.g. shortness of breath or snoring, in order, for example, to change the position of a back or foot part of the bed, as a result of which the person in the bed usually also changes their sleeping position. It may also be possible, for example, to temporarily switch on a lighting device coupled to the control unit of the furniture drive, e.g. a so-called floor lighting, if the evaluation and display unit 30 recognizes on the basis of the physiological data 12 that the person 4 has just left the bed.

The external devices 7 can be controlled from the evaluation and display unit 30 via control channel 33 via radio, e.g. BLUETOOTH® or WLAN, or via infrared control. This can be done directly or by integrating a building automation controller ("Smart Home") with which the external devices 7 are coupled.

Conversely, ambient data collected by the building automation and not measured by the sensor arrangement 20 can also be made available to the evaluation and display unit 30 for consideration.

What is claimed is:

1. A system for determining a value representing a sleep quality, said system comprising:
   a first sensor coupled to a piece of sleep or rest furniture and configured to determine physiological data of a person using the piece of sleep or rest furniture in response to a detection of a vibration, movement and/or sound;
   an evaluation device operably connected to the first sensor;
   a second sensor provided on the piece of sleep or rest furniture or in an ambient environment of the piece of sleep or rest furniture, said second sensor configured to detect an ambient parameter;
   an evaluation circuit configured to determine ambient data from a signal of the second sensor;
   a housing accommodating the second sensor and the evaluation circuit;
   a transmission unit accommodated in the housing and configured to output the ambient data; and
   an evaluation and display unit coupled to the evaluation device and the evaluation circuit and adapted to evaluate the physiological data and the ambient data to thereby determine the value representing the sleep quality.

2. The system of claim 1, wherein the second sensor is a temperature sensor, a humidity sensor, an airborne sound sensor or a brightness sensor.

3. A sensor arrangement for detecting an ambient parameter of a piece of sleep or rest furniture and physiological data of a person using the piece of sleep or rest furniture, said sensor arrangement comprising:
- a first sensor measuring the ambient parameter;
- an evaluation circuit evaluating a signal from the first sensor and configured to determine ambient data from the signal of the first sensor;
- a second sensor coupled to the piece of sleep or rest furniture and configured to determine the physiological data of a person using the piece of sleep or rest furniture in response to a detection of a vibration, movement and/or sound;
- an evaluation device operably connected to the second sensor;
- a transmission unit outputting the ambient parameter in the form of digital ambient data;
- a housing accommodating the first sensor, the evaluation circuit, and the transmission unit; and
- an evaluation and display unit coupled to the evaluation device and the evaluation circuit and adapted to evaluate the physiological data and the ambient data to thereby determine the value representing the sleep quality.

4. The sensor arrangement of claim 3, wherein the first sensor is a temperature sensor, a humidity sensor, an airborne sound sensor or a brightness sensor.

5. The sensor arrangement of claim 3, wherein the transmission unit is configured for wireless transmission of the digital ambient data.

6. The sensor arrangement of claim 3, wherein the transmission unit is configured for wireless transmission in accordance with a BLUETOOTH® and/or WLAN protocol.

7. A piece of sleep or rest furniture comprising:
- a system for determining a value representing a sleep quality,
- said system comprising a first sensor coupled to the piece of sleep or rest furniture and configured to determine physiological data of a person using the piece of sleep or rest furniture in response to a detection of a vibration, movement and/or sound,
- an evaluation device operably connected to the first sensor,
- a second sensor provided on the piece of sleep or rest furniture or in an ambient environment of the piece of sleep or rest furniture, said second sensor configured to detect an ambient parameter,
- wherein the system includes an evaluation circuit configured to determine ambient data from a signal of the second sensor,
- a housing accommodating the second sensor and the evaluation circuit,
- and a transmission unit accommodated in the housing and configured to output the ambient data,
- wherein the system includes an evaluation and display unit coupled to the evaluation device and the evaluation circuit and adapted to evaluate the physiological data and the ambient data to thereby determine the value representing the sleep quality.

8. The piece of sleep or rest furniture of claim 7, wherein the second sensor is a temperature sensor, a humidity sensor, an airborne sound sensor or a brightness sensor.

9. The piece of sleep or rest furniture of claim 7, further comprising a sensor arrangement for detecting the ambient parameter, said second sensor being part of the sensor arrangement, and the transmission unit outputting the ambient parameter in the form of digital ambient data.

10. The piece of sleep or rest furniture of claim 9, wherein the transmission unit is configured for wireless transmission of the digital ambient data.

11. The piece of sleep or rest furniture of claim 7, wherein the transmission unit is configured for wireless transmission in accordance with a BLUETOOTH® and/or WLAN protocol.

12. The piece of sleep or rest furniture of claim 7, constructed in the form of a bed.

13. The piece of sleep or rest furniture of claim 7, further comprising an electromotive furniture drive including a control unit and an adjusting drive.

14. The piece of sleep or rest furniture of claim 13, further comprising a sensor arrangement for detecting the ambient parameter, said second sensor being part of the sensor arrangement, and the transmission unit outputting the ambient parameter in the form of digital ambient data, wherein at least one of the evaluation device and the sensor arrangement is integrated into the control unit of the electromotive furniture drive.

* * * * *